United States Patent [19]

Repasky et al.

[11] Patent Number: 4,994,496

[45] Date of Patent: Feb. 19, 1991

[54] USE OF MILK GLOBULES AS CARRIERS FOR DRUGS

[76] Inventors: Elizabeth A. Repasky, 66 Frankhauser Rd., Williamsville, N.Y. 14221; Richard B. Bankert, 148 Capen Blvd., Amherst, N.Y. 14226

[21] Appl. No.: 94,515

[22] Filed: Sep. 9, 1987

[51] Int. Cl.$^5$ .................. A61K 9/127; A61K 35/20
[52] U.S. Cl. .................. 514/775; 424/439; 424/442; 424/450; 424/87; 424/94.3; 530/832
[58] Field of Search ................ 530/832; 424/439, 442, 424/87, 450, 94.3; 514/59, 775; 536/112

[56] References Cited

U.S. PATENT DOCUMENTS

| | | | |
|---|---|---|---|
| 1,302,487 | 4/1919 | Dunham | 514/775 |
| 2,023,125 | 12/1935 | Dryfuss | 514/775 |
| 2,194,188 | 3/1940 | Supplee | 530/832 |
| 2,300,410 | 11/1942 | Ferrari | 514/775 |
| 3,013,941 | 12/1961 | Gunderson | 514/775 |
| 3,072,533 | 1/1963 | Johnson | 424/439 |
| 3,553,317 | 1/1971 | Michaelson et al. | 530/832 |
| 3,608,064 | 9/1971 | Lamb | 424/439 |
| 4,293,654 | 10/1981 | Levine et al. | 536/112 |
| 4,324,782 | 4/1982 | Beck | 424/87 |
| 4,529,712 | 7/1985 | Jou et al. | 436/519 |
| 4,612,370 | 9/1986 | Hunt | 536/112 |
| 4,623,541 | 11/1986 | Elliot et al. | 530/832 |
| 4,636,384 | 1/1987 | Stolle et al. | 424/87 |
| 4,732,757 | 3/1988 | Stolle et al. | 424/87 |
| 4,777,162 | 10/1988 | Hijiya et al. | 424/439 |
| 4,784,850 | 11/1988 | Abraham | 530/832 |
| 4,879,110 | 11/1989 | Beck et al. | 424/85.8 |

OTHER PUBLICATIONS

Mather, I. H. and Kennan, T. W., Studies on the Structure of Milk Fat Globule Membrane., J. Membrane Biol., 21:65, 1975.

McPherson et al., Reviews of the Progress of Dairy Science: The Bovine Milk Fat Globule Membrane—its Formation, Composition, Structure and Behaviour in Milk and Dairy Products, J. Dairy Research (1983), 50:107–133.

Kobylka, D. and Carraway, K. L., Proteins and Glycoproteins of the Milk Fat Globule Membrane, Biochim. Biophys. Acta, 288:282, 1972.

Huang, C.-C., Tsai, C.-M. and Canellakis, E. S., Iodination of Cell Membranes. II. Characterization of HeLa Cell Membrane Surface Proteins. Biochim. Biophys. Acta, 332:59, 1973.

Anderson, M., Cawston, T. and Cheeseman, G. C., Molecular-Weight Estimates of Milk-Fat--Globule-Membrane Protein-Sodiumdodecyl Sulphate Complexes by Electrophoresis in Gradient Acrylamide Gels. Biochem. J. 139:653, 1974.

Jou, Y-H., Mazzaferro, P. K., Mayers, G. L. and Bankert, R. B., Methods for the Attachment of Haptens and Proteins to Erythrocytes. Methods in Enzymology 92:257, 1983.

Primary Examiner—Ronald W. Griffin
Attorney, Agent, or Firm—Scully, Scott Murphy & Presser

[57] ABSTRACT

This invention relates to a carrier for the transport of drugs in a mammalian system comprising milk fat globules.

8 Claims, No Drawings

USE OF MILK GLOBULES AS CARRIERS FOR DRUGS

FIELD OF THE INVENTION

This invention relates to a novel system for the delivery of drugs and more particularly is concerned with the use of milk fat globules as carriers for drugs.

BACKGROUND OF THE INVENTION

Selective action of drugs is an important prerequisite for their successful application in treating or preventing disease. However, because of the many similarities (e.g. in membrane structure and function, metabolic properties, etc.) which exist between the cells to be treated with the drug and normal cells, a specific effect is more often than not the exception rather than the rule. Consequently, side effects occur which hamper or even prevent treatment of a wide variety of diseases ranging from cancer to inherited metabolic disorders. A problem additional to that of poor drug selectivity, is the inability of certain drugs to reach diseased areas. For example, in many parasitic diseases, drugs cannot kill intracellular micro-organisms because of the protection offered to the parasites by cellular membranes in the form of permeability barriers to the drugs. Alternatively, drugs cannot reach the target mainly because of their large size. This is the case with enzymes which are potentially useful in the treatment of some enzyme deficiencies affecting the central nervous system but are unable to cross the blood-brain barrier.

The use of carriers for the transport of drugs to target areas is now recognized as a promising method of improving drug selectivity and action. Many types of carriers such as macromolecular cells, viruses and synthetic particles have been proposed.

It is, however, apparent that most known carriers are limited in the range and quantity of drugs which they can accommodate and also in their ability to prevent contact of their drug moiety with the normal biological environment or to promote its access to areas in need of treatment. In addition, there are difficulties related to the toxicity of the carrier's components, to their availability or cost and to the preparation of the carrier-drug unit. Consequently, extensive efforts have been made, especially in the last decade, towards the development of an ideal drug carrier. Such a carrier should be capable of delivering a wide variety of agents into the precise site of action within the biological entity with no untoward effects on the (normal) remainder of the entity.

The utility of any carrier system is determined by: (1) lack of cytoxicity, (2) biodegradability, (3) lack of immunogenicity (unless designed to specifically carry antigens), (4) the efficiency with which molecules and macromolecules are incorporated into the carrier under conditions that do not alter and/or inactivate the incorporated materials, (5) the ability to protect carrier-associated materials from alteration and/or breakdown by exposure to extracellular environment, and (6) the efficiency with which carrier-associated materials are transferred to cells.

The use of lipid vesicles (liposomes) for the delivery of drugs for both in vivo and in vitro studies is now in wide use since they consist of biodegradable lipid components in a spontaneously forming bilayer configuration, the composition of which can be varied to a marked extent. This variability allows the physical and chemical properties of liposomes to be altered and this can be exploited to alter their retention and uptake in vivo. Thus, the fixed charges on the liposome surface can be varied by incorporating long-chain, charged amphipaths such as fatty acids or naturally occurring negatively charged phospholipids.

Two important potential uses of such carrier-entrapped drugs in vivo are: (1) they could be used as a means for controlled release of small quantities of drugs over long periods of time, possibly also associated with decreased metabolic breakdown of the trapped drug, and (2) they could function to direct drugs to particular tissues.

Since many cancers are resistant to chemotherapy, it would be of great importance if a carrier could be devised as a means of increasing the effectiveness of anti-cancer drugs by exploiting one or the other of the properties mentioned above. This would be a clear advantage to the carrier-entrapped drugs since the pharmacokinetics of the drug need not be altered by chemically modifying the drug, which may in turn modify its biological effect, but by altering the composition of the drug carrier.

BRIEF SUMMARY OF THE INVENTION

We have now discovered a novel carrier for drugs which possesses the foregoing advantageous properties. Specifically, the preferred carrier is milk fat globules (MFG) which comprise the cream fraction of milk and consist of fat droplets which are stabilized by an external membrane derived mainly from the apical plasma membrane of mammary secretory cells. The milk fat globules thus provide a natural, abundant and inexpensive carrier with the desired characteristics that readily permits the incorporation of drugs.

The MFG is especially useful in the delivery of fat soluble substances and can be used in the same manner as liposomes, i.e. in undirected and immunospecifically directed delivery protocols. The advantages of the novel carrier of the present invention include protection of the drug from the recipient, protection of the recipient from the drug, delivery of a larger payload, the lipid content of the MFG provides a stable vehicle for fat soluble drugs, the MFG can be size selected from 1 to 10 $\mu$m and the MFG is cost effective.

Moreover, fat soluble drugs are readily loaded either in vitro or in vivo into the densely packed lipid of the milk fat globule. The novel drug-MFG complex can be used to deliver drugs topically, orally or parenterally and antigens and antibodies can be covalently coupled to the surface of the drug-MFG complex to direct their binding and delivery of their contents.

DETAILED DESCRIPTION OF THE INVENTION

In our copending application Ser. No. 094,520, filed concurrently herewith entitled "MICROFLOTATION DEVICES USED FOR IMMUNOASSAYS AND CELL/MOLECULAR FRACTIONS" we have described a novel flotation immunoassay composed of milk fat globules bearing a proteinaceous layer capable of coupling with an antigen or an antibody and which may be used to separate bound and free products of the assay by floating to the surface of the reaction liquid.

As therein described, the milk fat globules consist of a triglyceride core surrounded by a lipid bilayer containing integral membrane proteins. Mather and Keenan, J. *Membrane Biol.* 21: 65, 1975. The globules range in size from 1 to 10 μm diameter surrounded by a thin membrane called the milk fat globule membrane (MFGM). This membrane (approximately 10 nm in cross-section) consists of a complex mixture of proteins, phospholipids, glycoproteins, triglycerides, cholesterol, enzymes and other minor components. McPherson, et al. *J. Dairy Research* (1983) 50:107-133. Studies of the membrane proteins have revealed that several of these are glycoproteins and that the proteins are asymmetrically arranged in the membrane such that portions of them are exposed on the external surface of the MFG. Kobylka, et al., *Biochim. Biophys. Acta* 288: 282, 1972, Huang, et al., *Biochim. Biophys. Acta* 332: 59, 1973 and Anderson, et al., *Biochem. J.* 139: 653, 1974.

The milk fat globules consist of 99% triglycerides which are synthesized in the mammary gland secretory cell from precursors in the blood (i.e. glucose, acetate, low density lipoproteins). This high lipid content makes the MFG an ideal vehicle for the loading of fat soluble drugs.

The fat soluble drugs may be loaded either in vitro or in vivo into the densely packed lipid of the milk fat globule. The drugs may be loaded into the MFG in vitro simply by stirring the drug in a suspension of milk fat globule for approximately 18 hours at 25° C. The time and temperature are not critical and may vary from 18° C. to 37° C. for a time period of from 12 hours to 24 hours. It suffices merely that the drug be rapidly and stably loaded into a suspension of milk fat globules by contacting the reactants for the requisite period of time and at an appropriate temperature.

The fat soluble drug appears to concentrate within the fat depot of the MFG. The drug loaded MFG is storage-stable at room temperature for a week or more.

The drug may also be loaded into the MFG containing an antigen coupled to the proteinaceous surface and prepared as described in our aforesaid copending application.

Thus an antigen such as dextran may be coupled to the glycoproteins of the MFG by a variety of chemical techniques as, for example, the techniques described by Jou, et al. *Methods in Enzymology*, Vol. 92:257-275(1983), which is incorporated herein by reference.

As therein described, a preferred method attaches the antigen to the surface of a cell without a covalent bond to the membrane molecules. A lipopolysaccharide, myristol-oxidized dextran (MOD) has been designed to which haptens and protein can be covalently coupled. The antigen-MOD directly attaches to the surface of the cells via a stable hydrophobic interaction with the plasma membrane. It is believed that the antigen-MOD is attached to the surface of cells via the intercalation of the lipid moiety of the lipopolysaccharide into the hydrophobic portion of the plasma membrane. The covalent attachment of haptens and proteins to the MOD occurs between free amino groups present on the haptens or proteins and reactive aldehyde groups on the MOD. The synthetic lipopolysaccharide can, therefore, be used as a general method for coupling haptens or proteins to cells or antigens.

It is also possible to load the fat soluble drugs into the MFG in vivo by administering the drugs to lactating mammals but this is not preferred.

Typical fat soluble drugs that may be used to load MFG according to the present invention include cytotoxic drugs such as adriamycin, daunomycin, melphalan and podophyllotoxin, vitamins, such as vitamin D and vitamin E, steroids, such as cortisol, estradiol, testosterone and progesterone, and fat soluble antibiotic derivatives.

The invention will be described in greater detail in conjunction with the following specific examples.

EXAMPLE 1

The milk fat globules to be loaded with drug are obtained from raw bovine milk by centrifugation at 1,500×g for 10 min at room temperature followed by removal of the underlying (sub-natant) aqueous material. The MFG is washed three times by the addition of phosphate buffered saline, pH 7.4 (PBS) to the original volume followed by centrifugation at 1500×g for 10 min and removal of the sub-natant fluid. Adriamycin is rapidly and stably loaded into the MFG very efficiently by incubating 0.9 ml packed MFG with 0.1 ml adriamycin, dissolved in PBS to a concentration of 1 mg/ml, overnight at room temperature. The resultant MFG is then transferred to a 10 ml syringe fitted with a stopcock, brought to 10 ml with PBS and centrifuged at 1500×g for 10 min. The sub-natant fluid is removed by opening the stopcock and the milk fat globule layer is washed three times by gentle suspension in PBS followed by centrifugation. The final milk fat globule layer is brought to a final concentration of 20 percent (v/v) by the addition of approximately 4 ml PBS for storage at room temperature. The presence of adriamycin is detected in the MFG by its fluorescence emission at 590 nm using fluorescence microscopy. Alternatively, the amount of incorporated adriamycin can be calculated by difference, after determination of the amount of adriamycin remaining in the first sub-natant fraction by spectrofluorometric determination using an excitation wavelength of 470 nm and an emission wavelength of 590 nm. The drug appears to concentrate within the fat depot of the MFG, and up to 80 percent of the added drug is incorporated into the MFG. Drug loaded MFG can be stored at room temperature for at least seven days without loss of drug. It can be sterilized prior to injection by gamma irradiation.

EXAMPLE 2

The procedure of Example 1 is followed except that the adriamycin is loaded into the MFG to which an antigen or antibody is covalently linked. In this instance, the antigen or antibody is first coupled to the MFG preferably as described in our aforesaid copending application.

In this example, dextran is coupled to MFG as described in Example 1 of our aforesaid copending application, followed by loading with adriamycin as described in Example 1 hereinabove. The MFG is diluted in PBS to a concentration of $2 \times 10^8$ MFG/ml after counting using an inverted microscope and inverting the hemacytometer to allow the MFG to float to the grid. Mice are injected intraveneously via the tail vein with 0.5 ml of this suspension. Five days later, the animals are challenged by intra-peritoneal injection with 100 μg dextran in complete Freund's adjuvant. Six days later, the animals are sacrificed, their spleens removed and assayed for anti-dextran plaque-forming cell responce. It is found that a 95 percent reduction in the anti-dextran response occurs in animals treated with adriamycin loaded dex-MFG when compared with untreated animals. Thus, it appears that specific targetting of adriamycin loaded MFG to cells which bind dextran occurs.

What is claimed is:

1. A therapeutic composition of matter comprising milk fat globules which are surrounded by a lipid bilayer containing proteins and glycoproteins and loaded with therapeutic agent other than milk fat.

2. A composition of matter according to claim 1 in which the therapeutic agent is toxic to or modulates the growth or function of cells or pathogens.

3. A composition of matter according to claim 1 in which the therapeutic agent is a drug, nutrient, antimetabolite, antibody, enzyme, growth factor or nucliec acid.

4. A composition of matter according to claim 1 in which an antigen or antibody is coupled to the milk fat globules.

5. A method of administering a therapeutic agent to a mammal which comprises loading a therapeutic agent into milk fat globules which are surrounded by a lipid bilayer containing proteins and glycoproteins and then administering the milk fat globule therapeutic agent unit into said mammal, topically, orally or parenterally.

6. A method of loading a therapeutic agent into milk fat globules which are surrounded by a lipid bilayer containing proteins and glycoproteins in vitro which comprises incubation of the milk fat globules with the therapeutic agent.

7. A method of loading a therapeutic agent into milk fat globules in vivo which comprises administering the therapeutic agent to a lactating mammal and collecting milk from said mammal thus providing milk fat globules loaded with the therapeutic agent.

8. A method for loading a therapeutic agent into milk fat globules which comprises incubation of mammary cells in culture with the therapeutic agent and collection of the milk fat globules made by the cells.

* * * * *